United States Patent [19]

Richter

[11] Patent Number: 4,961,726
[45] Date of Patent: Oct. 9, 1990

[54] BREAST MILK PUMP

[76] Inventor: Siegfried Richter, Rudolfstrasse 3, D-7798 Pfullendorf, Fed. Rep. of Germany

[21] Appl. No.: 291,001

[22] Filed: Dec. 28, 1988

[51] Int. Cl.⁵ .............................................. A61M 1/06
[52] U.S. Cl. .................................... 604/74; 604/313; 604/346
[58] Field of Search .................. 104/74, 75, 313, 346; 119/14.05, 14.06, 14.07, 14.08; 604/74, 73, 313, 346

[56] References Cited

U.S. PATENT DOCUMENTS

| 4,323,067 | 4/1982 | Adams | 604/74 |
| 4,886,494 | 12/1989 | Morifuji | 504/74 |

FOREIGN PATENT DOCUMENTS

| 0123269 | 10/1984 | European Pat. Off. | |
| 2812830 | 8/1387 | Fed. Rep. of Germany | |
| 2241233 | 9/1980 | Fed. Rep. of Germany | |
| 3314942 | 10/1980 | Fed. Rep. of Germany | 604/346 |
| 3219628A1 | 12/1983 | Fed. Rep. of Germany | |
| 462588 | | U.S.S.R. | |

Primary Examiner—J. L. Kruter, Jr.
Attorney, Agent, or Firm—McGlew & Tuttle

[57] ABSTRACT

A breast milk pump suction arrangement includes a suction pump with suction connections, a fellow breast connector, a reservoir connected to the funnel and a pulsator. The suction pump is connected to the pulsator by a first suction line and a reservoir is connected to the pulsator by a second suction line. The pulsator includes a cylindrical housing supporting a control element which is moveable within said cylinder. The control element defining an air chamber and a vacuum chamber. The vacuum chamber being in communication with the first suction line and the second suction line. An opening in said cylinder providing communication between said air chamber and atmosphere. An air intake valve is provided to vent the vacuum chamber to atmosphere periodically by opening and closing a valve closing element. A transmission arrangement is provided, connecting the control element and the valve element. The transmission arrangement includes a delay for delaying the closing of the valve element upon movement of the control element in a closing direction.

14 Claims, 2 Drawing Sheets

BREAST MILK PUMP

FIELD OF THE INVENTION

The invention relates to a breast milk pump with an electrically actuated suction pump, which is connected by a suction line to a suction funnel via at least one collecting container and whose suction flow is rhythmically interrupted by means of a periodically operating valve to provide a pulsating suction effect at the suction funnel.

BACKGROUND OF THE INVENTION

In the breast milk pumps of the above kind known so far, the periodical opening and closing of the valve interrupting the suction flow is controlled by an electronic pulse generator. Herein electromagnetic valves are controlled by the control laid out respectively so that they open and close periodically to generate a pulsating suction effect.

In mechanical milkers for cattle so-called vacuum pulsators are used (See for example DE-AS 22 41 233, DE-OS 32 19 628, DE-PS 28 12 830), but their operational principle cannot be applied to a breast milk pump of the same kind as in these mechanical milkers the so-called milking cup (teat rubber) has two vacuum lines for each milking cup which have to be controlled by means of separate, but interacting valves. A known breast milk pump (EP 01 23 269 A2) is too awkward and too expensive for private use with its pneumatically actuated pump piston which is controlled by two valves.

SUMMARY AND OBJECTS OF THE INVENTION

The invention is based on the task of improving a breast milk pump of the kind initially mentioned so that the suction flow pulsating at the suction funnel is generated in a less expensive manner and is simpler, maintenance- and trouble-free.

According to the invention the task is solved as follows. The vacuum chamber of the pulsator in the suction line forms a connection, which is open at both ends and cannot be closed, between the suction pump and a reservoir. The control element separating the air chamber from the vacuum chamber opens an air intake valve connecting the vacuum chamber with the atmosphere at the end of the control elements forward movement caused by the evacuation of the vacuum chamber, and the closing element of the air intake valve is returned to its closed position with delay either by the control element at the end of its return movement delayed by throttle nozzles or by its return spring and a delay element influenced by a throttle nozzle.

A breast milk pump according to the above specifications has the advantage that it does not require an electromagnetic valve or electronic control device to generate a periodical pulsating suction flow at the suction funnel. Instead, only a single, simple valve operating entirely pneumatic-mechanically, which is, in addition, relatively small and can be manufactured inexpensively. If e.g. for safety reasons two reservoirs are arranged in series in the suction line, it is possible to arrange the pulsator between the two containers in the suction line.

The control element of the valve can comprise a piston moving axially in a cylinder. According to one feature of the invention the control element comprises a piston which is arranged axially movable in a cylinder, the piston being connected through an axial driving rod with the closing element of the air intake valve. Alternatively, the air intake valve comprises a seal ring, which is arranged concentrically to the air intake duct on the face side of the shutting element and also a valve head fixed on the driving rod. The control element may be essentially a disc—or plate shaped membrane such as a spring-elastic with a central valve opening, which is closed from the direction of the vacuum chamber by a closing element, which is kept in the closed-position by an axial spring force working in direction of the air chamber and which is in connection with a movement throttle and bellows through a rod whose diameter is smaller than the diameter of the valve opening.

According to one embodiment of the invention a piston is used as the control element, the arrangement of the air intake valve is especially simple and safe. By the driving rod being movably connected to the piston between two axial catches, and the opening of the air intake valve, surge is achieved. By providing the driving rod with a second spring working in the opening direction of the closing element friction between the driving rod and the piston is compensated and the combined spring force influencing the driving rod in the opening direction of the closing element is made smaller than the maximal atmospheric pressure of the closing element to make sure that the desired working rhythm of the air intake valve cannot be impeded by the bearing friction between the driving rod and the piston. Furthermore it serves the increase of operational safety insofar as the spring forces influencing the closing element are practically without effect in the closed state of the air intake valve.

By providing a prestressed return spring, with a piston which may be changed by axially repositioning a spring support surface in the cylinder it is easy to change the working rhythm of the pulsator.

By providing the air chamber with an opening to atmosphere including a discharge throttle nozzle which is closed by a spring-biased throttling element pressed against the opening in the intake direction additional options are provided to influence the working rhythm of the air intake valve, in particular the relation between opening time and closing time.

By providing the air chamber with an air intake valve which is self-closing in the discharge direction, and whose discharge diameter is larger than the diameter of the discharge throttle nozzle it is possible to ensure that the opening movement of the air intake valve depends exclusively on the strength of the suction flow in the vacuum chamber, while the closing movement depends exclusively on the strength of the return spring and the throttle effect of the throttle nozzle.

By positioning the piston rod such that it passes through a central axial bore of the piston and through a bore in the valve shutting element, coaxial thereto, so as to close the vacuum chamber of the cylinder at the face end, the bore of the shutting element taking at least partly the form of an air intake duct, an advantageous construction and simple mounting are achieved.

By providing the valve shutting element of the cylinder with two tube connection nipples (sealing members), both of which are connected to the air intake duct of the air intake valve and/or to the vacuum chamber a advantageous construction is provided with simple mountability and superior operational safety.

By the providing the air intake valve with a seal ring, which is arranged concentrically to the air intake duct on the face side of the shutting element and also a valve head fixed on the driving rod better mountability and superior operational safety are achieved.

Providing a control element separating the air chamber from the vacuum chamber which is a spring-elastic and essentially disc-shaped membrane with a central valve opening, which is closed from the direction of the vacuum chamber by a closing element, which is kept in the closed-position by an axial spring force working in direction of the air chamber and which is in connection with a movement throttle through a rod whose diameter is smaller than the diameter of the valve opening results in many advantages including simplicity and fewer operating parts. These advantages are further brought out by using a movement throttle comprising a bellows, whose inner chamber is connected to the atmosphere through an air throttling nozzle and employing a pulsator with two housing parts joined on the clamping level of the membrane edge, one housing part forming the vacuum chamber having two tube connection nipples and the other housing part having at least one air intake opening and an air throttle nozzle opening into the bellows.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which a preferred embodiment of the invention is illustrated.

DETAILED DESCRIPTION OF THE REFERRED EMBODIMENTS

Figure 3:
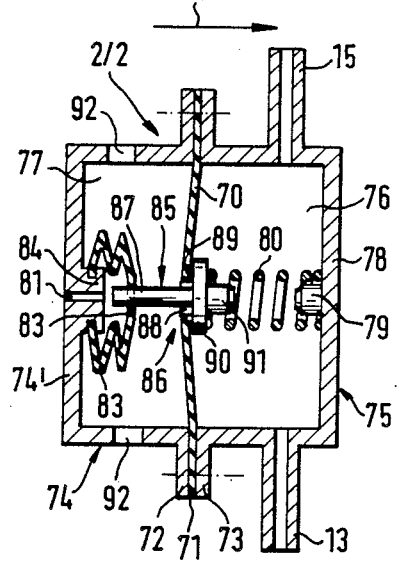
FIG. 3 is a section of a further pulsator for the breast milk pump in FIG. 1, showing the closed position of its air intake valve.
Figure 4:
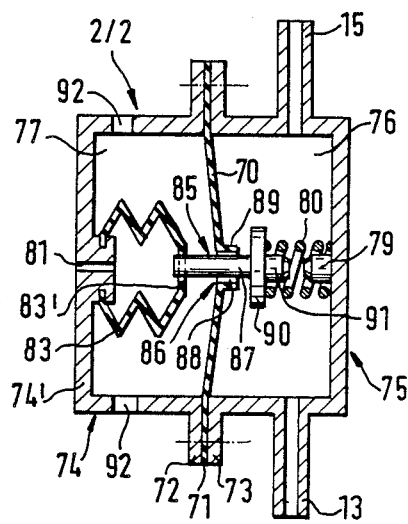
FIG. 4 shows the section of the pulsator of FIG. 3, showing the open-position of its air intake valve.

Referring to the drawings in particular, the invention comprises a suction pump arrangement including a suction pump 1, a funnel breast connector 4, a reservoir 3 connected to the funnel and a pulsator 2. The suction pump is connected to the pulsator by a first suction line 16. A reservoir is connected to the pulsator by a second suction, line 12. The pulsator advantageously comprises a housing 17 (FIG. 1); 17/1 (FIG. 2) 74, 75 (FIGS. 3 and 4) with a control element 20 (FIG. 1); 20/1 (FIG. 2); 70 (FIGS. 3 and 4) movably positioned in the housing and cooperating with the housing to define an air chamber 22 (FIGS. 1 and 2), 77 (FIGS. 3 and 4) and a vacuum chamber 21 (FIGS. 1 and 2), 76 (FIGS. 3 and 4). The vacuum chamber communicates with the first suction line and communicates with the second suction line. The housing is provided with at least one opening 23, 59, 92 communicating with atmosphere. An air intake valve 38, 86 is provided including an air intake valve opening 37, 88 and valve closing element 39, 90. The valve closing element is moveable to open and close the valve opening to allow and prevent communication between the vacuum chamber and atmosphere. Transmission means 26, 43, 44, 29, 28, 32 (FIGS. 1 and 2); 89 (FIGS. 3, 4) is provided connected between the control element and the air intake valve element for opening and closing the valve element upon movement of the control element in an opening and closing direction. The transmission means includes delay means 30, 28, 29, 32, 23 (FIGS. 1, 2); 83, 81 (FIGS. 3, 4) for delaying the closing of the valve element upon movement of the control element in the closing direction.

Figure 1:
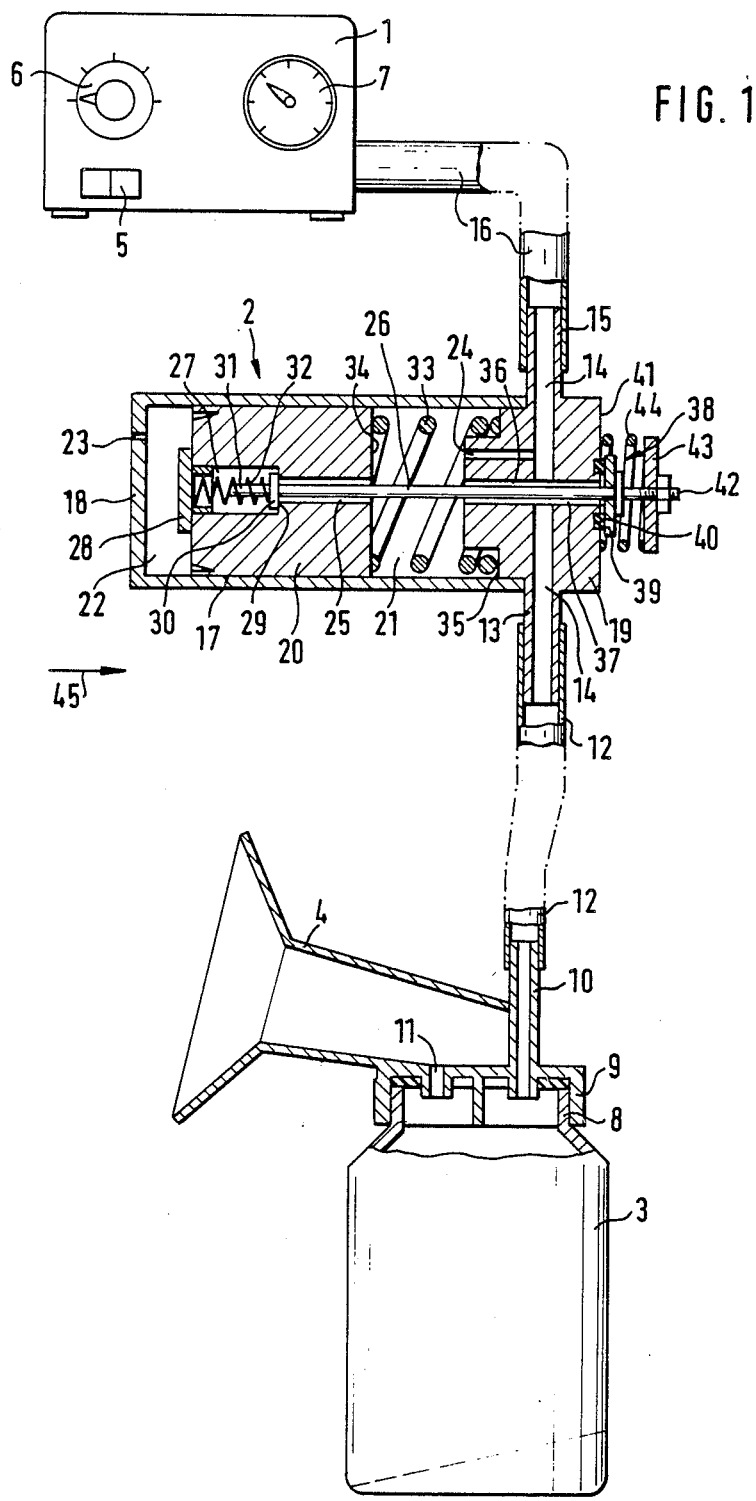
FIG. 1 shows a schematic representation of a breast milk pump with a pulsator and a suction funnel in sectional representation.

The breast milk pump in FIG. 1 comprises a pump unit 1, a pulsator 2, a bottle-shaped reservoir 3 and a suction funnel 4 mounted to it. The pump unit comprises an electric suction pump, which may be switched on and off by means of a switch 5 and whose suction output can be adjusted by means of a pump suction selector 6. The suction level is indicated on a manometer 7. The suction funnel 4 is formed onto the lid 9 preferably in a one piece construction. The lid may be mounted and sealed tightly to the neck 8 of the reservoir 3. The lid also comprises a tube connection nipple 10 which runs axis-parallel with a central axis of the lid, and runs parallel with an opening 11 connecting the inner chamber of the reservoir 3 with the inner chamber of the suction funnel 4. The inner chamber of the reservoir 3 is connected to the connecting nipple 13 of the pulsator 2 via the connecting nipple 10 and a tube 12. The pulsator 2 is directly connected to the suction side of the suction pump of the pump unit through a connecting duct 14, a second nipple 15 and a further tube 16. The pulsator has the task of periodically interrupting the continuous suction flow produced by the pump unit 1 so that a pulsating suction effect is generated in the suction funnel 4. The pulsator 2, is shown over dimensioned in relation to the size of the pump unit 1 only to make it easier to read the figure. In practice the pulsator 2 may be integrated in the housing of the pump unit 1.

According to the embodiment shown in FIG. 1 the pump unit comprises a cylinder 17 with a solid front wall 18 and a tight sealing shutting element 19 on the opposite front end. The shutting element includes the two nipples 13, 15 and the connection duct 14. A control element 20 which seals a vacuum chamber 21 air tightly from an air chamber 22 is provided as a piston which can be moved axially in the cylinder 17. The air chamber 22 is connected to the atmosphere through a throttle nozzle 23. The connecting duct 14 in the shutting element 19 is constantly connected to the vacuum chamber 21 by an axial bore 24.

The piston 20 has a central and axial bore 25 in which a driving rod 26 can move in an axial direction. The driving rod 26 is followed by a cylindrical recess 27 with a larger diameter, which is tightly closed at the front by a fixed cover 28. The shoulder ring between the recess 27 and the axial bore 25 forms an axial catch or stop 29 for a flange 30 of the driving rod 26, which has a coaxial extension 31 about half the length of the recess 27 and following the ring flange 30. A pressure spring 32 between the ring flange 30 and the cover 28 presses the flange ring 30 against the catch or stop 29. As the extension 31 of the driving rod 26 is only half as long as the recess 27, the driving rod 26 can move with regard to the piston 20 over half the length of the recess 27, until the front-facing end of the extension 31 touches the cover 28, which therefore forms the second axial catch or stop for the driving rod 26 in the piston 20. On the side opposite the cover 28 and the air chamber 22, i.e. in the vacuum chamber 21 a pressure spring 33 is mounted which touches the face 34 of the piston 20 on one side and on the ring shoulder 35 of the shutting element 19 on the other side. It pushes the piston 20 in the direction of the air chamber 22.

The piston rod 26 also goes through a central and axial bore 36 of the shutting element 19, in which it is axially movable. However, the piston rod can also be shaped so that a flow connection between the connecting duct 14 and the vacuum chamber 21 is generated. A cylindrical air intake duct 37 is arranged coaxially to the axial bore 36 of the shutting element 19. The air intake duct 37 is formed such that the driving rod 26 and is closable by means of a air intake valve 38. This air intake valve 38 comprises a valve head 39 which is fixed to the driving rod 26 passes through it and a valve seat which consists of a seal ring 40 arranged concentrically with regard to the air intake duct 37 on the outer face end 41 of the shutting element 19. A support disc 43 is fastened to an extension 42 of the driving rod 26 protruding from the valve head 39 to the outside. A pressure spring 44 sits between the support ring 43 and the face 4 of the shutting element 19. This pressure spring is relatively weak and serves only to overcome or compensate for the friction possibly existing between the piston 20 and the driving rod 26. Thus the driving rod 26 is not moved with the piston 20 at all times in the closing direction of the air intake valve 38. The two pressure springs 32 and 44 exert force in the opening direction of the air intake valve 38 on the driving rod 26, which is considerably smaller than the closing pressure working on the valve head from the opposite direction, when the pressure in the connection duct 14 and in the air intake duct 37 connected with it is low.

The pulsator 2 operates as follows:

The position of the piston 20 in the cylinder 17 is the starting position. Herein the valve head 39 is pressed tightly onto the seal ring 40 through the pressure spring 33 and the flange ring 30 of the piston rod 26 sitting on the axial catch 29. If a vacuum is formed in the vacuum chamber 21 while the pump unit 1 is working and the suction funnel sits on the mother's breast, the piston 20 is moved in one direction of the arrow 45 by the pressure in the air chamber 22. The driving rod 26 remains in the closing position of the valve head 39 due to the atmospheric pressure until the extension 31 touches the cover 28 working as a catch or stop. When the piston 20 moves on, the piston rod or driving rod 26 is carried along in the direction of the arrow 45 and the valve head 39 is lifted from the seal ring 40, and the air intake valve 38 opens. Herein the pressure spring 32 lets the driving rod 26 with the valve head 39 open in a surge. Through the opened air intake valve 38 air can enter the vacuum chamber 21 via the air intake duct 37, the connection duct 14 and the axial bore 24, resulting in a breakdown of the vacuum in the vacuum chamber 21 and also in the tube 12, the suction funnel 4 and the reservoir 3. During the piston movement in direction of the arrow 45 the pressure spring 33, which has a certain tension anyway, has been tension-loaded even more. This results in a return movement of the piston 20 against the direction of the arrow 45. This return movement, however, is slowed down by the breaking effect of the throttle nozzle 23. As the pressure spring 32 has pushed the flange ring 30 against the catch 29 again while the air intake valve 38 was opened, the piston rod 26 is carried along in closing direction by the piston 20 in its return movement. The movement of the piston 20 stops as soon as the valve head 29 sits on the seal ring 40 again. A new cycle begins. A vacuum is generated in the vacuum chamber 21 and in the reservoir as well as in the suction funnel 4, with the result that the piston moves again in the direction of the arrow 45 and executes the functions described above.

Figure 2:
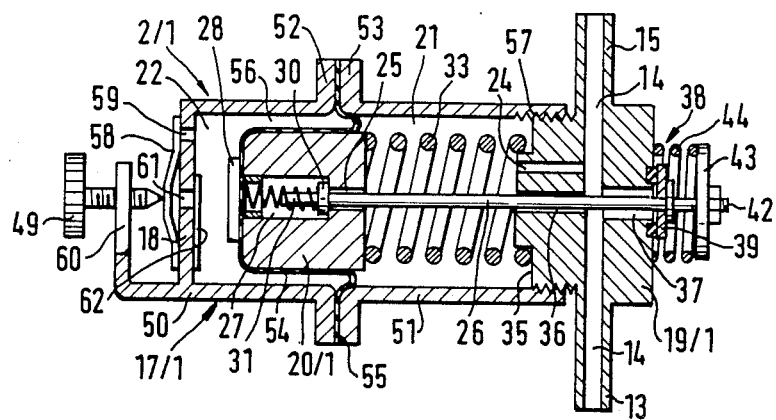
FIG. 2 is a section of another pulsator for the breast milk pump in FIG. 1.

In the pulsator 2/1 in FIG. 2 the cylinder 17/1 is assembled from two cylinder parts 50 and 51, which are connected to one another by two connection flanges 52 and 53. Herein the outer diameter of the piston 20/1 is considerably smaller than the inner diameter of the cylinder 17/1, so that an annular gap 56 is formed between the two. In order to separate the vacuum chamber 21 air-tightly from the air chamber 22, the piston 20/1 is equipped with an envelope membrane 54, whose edge 55 is clamped between the connection flanges 52 and 53. Otherwise the piston 20/1 corresponds to the piston 20 of the pulsator 2. The axial bore 25 as well as the recess 27 and the cover 28 are present, and so are the piston rod 26 and the air intake valve 38. The shutting element 19/1 is different from the shutting element 19 only in that it is can be screwed into the open face of the cylinder element 51 by means of a thread 57, and that it can be axially adjusted. Thus the prestress of the pressure spring 33 and therefore the velocity of the piston movement 20/1 in direction of the arrow 45, i.e. in the opening direction of the air intake valve 38 can be adjusted by the thread 57.

While the cylinder 17 has merely an non changeable throttle nozzle 23 in the form of an axial bore in the face wall 18, the cylinder element 50 has a throttle nozzle 59 in its face wall, which is closed on the outside by a biassed leaf spring 58. Through this throttle nozzle 59 the air from the air chamber 22 can be discharged during the return movement of the piston 20/1 at a determined velocity. The closing pressure of the feather element 58 working as a throttle element, can be adjusted by means of a set screw 59 on a shackle 60. Thus the discharge velocity of the air through the throttle nozzle 49 can be affected, and therefore the velocity of the piston 20/1 return movement can be manipulated. A special air intake valve is used for the air flowing into the air chamber 22. It comprises a central and axial bore 61 in the face wall 18 and a closing flap 62, which is arranged on the inside of the face wall 18 and which closes the bore 61 in the escape direction. Aside from the fact that the piston can be manipulated by changing the prestress of the pressure spring 33 and the prestress of the leaf spring 58 covering the throttle nozzle 59, the operation of the pulsator 2/1 corresponds to the operation of the pulsator 2.

For reasons of economy all parts with the exception of the pressure springs 32, 33 and 44 can be manufactured from plastic.

In the pulsator represented in FIG. 3 and 4 the control element replacing the piston 20 resp. 20/1 consists of an elastic membrane 70 whose edge 71 is clamped air-tightly between the connection flanges 72 and 73 of two cylindrical housing parts 74 and 75. The two housing parts 74 and 75 are arranged coaxially to one another and they have the same inner diameter. Through the membrane 70 their common inner chamber is subdivided into a vacuum chamber 76 and an air chamber 77. The housing part 75 containing the vacuum chamber 76 has two connection nipples 13 and 15 for the tubes 12 and 16. The face wall 78 of the housing part 75 is completely closed, having a guiding peg 79 for the pressure spring 80 at its center on the inside. The face wall 74' of the housing part 74 has a throttle nozzle 81 connecting the atmosphere with the inner chamber of a bellows 83, which is fastened to a cylindrical nipple 84 on the inside of the face wall 74' and which is connected to a closing element 85 of an air intake valve 86. This closing element 85 consists of a cylindrical rod 87 fastened to the closed face wall 83' of the bellows 83 protruding through a central valve opening 88 of the membrane having a larger diameter than the cylindrical rod 87, which has a valve head 90 which sits tightly sealing on the edge bead 89 of the opening 88. The edge bead 89 and the valve head 90 are located in the vacuum chamber 76. On the side facing the face wall 78 of the housing part 75 the valve head 90 has a guide peg 91 for the pressure spring 80, which presses the closing element 85 into its closed-position, in which the valve head 90 sits tightly sealing on the edge bead 89.

This pulsator 2/2 can replace the pulsator 2 resp. 2/1 without problems in the milk pump shown in FIG. 1. It operates as follows:

From the home position (initial position) of the membrane 70, in which the valve head 90 sits tightly sealed on the edge bead 89, i.e. the air intake valve 86 is closed, the valve head 70 is moved into the direction of the arrow 45 as the vacuum in the vacuum chamber 76 increases. The velocity of the movement is herein reduced due to the action of the pressure spring 80 and the throttling effect of the air throttling nozzle 81, through which air is sucked into the bellows 83 air chamber. This movement of the membrane 70 in direction of the arrow 45 is continued to the point at which the membrane 70 has reached its extreme position in opposite direction represented in FIG. 4. Herein, however, the movement of the closing element 85 is not stopped, but is continued in the same direction, so that the valve head 90 is lifted from the edge bead 89 off the membrane 70, i.e. the air intake valve 86 is opened. This sole movement of the closing element 85 is the result of the pressure differences in the vacuum chamber 76 and the air chamber 77 and of the fact that the rod 87 of the closing element 85 has a smaller diameter than the valve opening 88, through which the atmospheric pressure in the air chamber 77 can have an effect on the valve head 90.

Due to the air flowing from the air chamber 77 through the open air intake valve 86 into the vacuum chamber 76 an equalization of pressure, i.e. a vacuum breakdown takes place for a short while. As soon as the air intake valve 86 is open, the membrane 70 springs back into its home position of FIG. 3. Due to the throttling effect of the throttle nozzle 81 and the bellows 83 the closing element 85 cannot follow the return movement of the membrane 70 at the same velocity. The return movement of the closing element 85 is therefore correspondingly slower, so that between the opening and the closing of the air intake valve 86 a delay takes place which depends on the strength of the pressure spring 80 and on the diameter of the throttle nozzle 81 and which determines the pulse frequency of the pulsator 2/2. When the closing of the air intake valve 86 is finally effected through a tight sealing of the valve head 90 on the edge bead 89, a new pulsation cycle begins in the fashion described above with the building-up of a vacuum in the vacuum chamber 86.

In the pulsator 2/2 the prestress of the pressure spring 80 can be changed by adequate means just as in the pulsator 2/1. Also, the throttle nozzle 81 can be changed as in the pulsator 2/1 by using a feather element, and therefore by influencing the delay. While specific embodiments of the invention has been shown and described in detail to illustrate the application of the principals of the invention, it will be understood that the invention may be embodied otherwise without departing from such principals.

What is claimed is:

1. A breast milk suction pump arrangement comprising: a suction pump having a suction connection; a funnel breast connector; a reservoir connected to said funnel; and a pulsator, said suction pump being connected to said pulsator by a first suction line, said reservoir being connected to said pulsator by a second suction line, said pulsator comprising a cylinder, a control element movably positioned in said cylinder and cooperating with said cylinder to define an air chamber and a vacuum chamber, said control element separating said air chamber and said vacuum chamber, said vacuum chamber communicating with said first suction line and communicating with said second suction line, said cylinder defining an opening allowing communication between said air chamber and atmosphere, an air intake valve including an air intake valve opening and a valve closing element, said valve closing element being movable to open and close said valve opening to allow and prevent communication between said vacuum chamber and atmosphere, transmission means connected between said control element and said valve element for opening and closing said valve element upon movement of said control element in an opening and closing direction, said transmission means including delay means for delaying the closing of said valve element upon movement of said control element in a closing direction, whereby said control element moves in an opening direction due to a vacuum generated in said vacuum chamber by said suction pump, thereby providing a pulsating suction action at said funnel breast connector.

2. A breast milk pump according to claim 1, wherein: said delay means includes a discharge throttle nozzle positioned in said opening allowing communication between said air chamber and atmosphere and an intake valve positioned adjacent said discharge throttle nozzle, said air intake valve being self closing in a discharge direction and having a discharge diameter which is larger than the diameter of the opening of said discharge throttle nozzle.

3. A breast milk pump according to claim 1, wherein: said control element includes an elastic substantially disk shaped membrane, said air intake valve opening being formed in said membrane by a central valve opening, said central valve opening being closed on a vacuum chamber side by a closing element, a spring positioned in said vacuum chamber urging said closing element into a closed positioned, said delay means including a bellows connected to said closing element through a rod, said rod having a diameter smaller than the diameter of said air intake valve opening.

4. A breast milk pump according to claim 3, wherein: said bellows defines an inner chamber connected to atmosphere through an inner chamber throttling nozzle.

5. A breast milk pump according to claim 4, wherein: the pulsator is formed of two housing parts, an edge of said membrane being positioned between said two housing parts, the first housing part cooperating with said membrane to define the vacuum chamber, said first housing parts having two connections, a second housing part having at least one air intake opening and an inner chamber air throttling nozzle opening into said inner chamber.

6. A breast milk suction pump arrangement comprising: a suction pump having a suction connection; a funnel breast connector; a reservoir connected to said funnel; and a pulsator, said suction pump being connected to said pulsator by a first suction line, said reservoir being connected to said pulsator by a second suction, said pulsator comprising a cylinder, a control element movably positioned in said cylinder and cooperating with said cylinder to define an air chamber and a vacuum chamber, said control element separating said air chamber and said vacuum chamber, said vacuum chamber communicating with said first suction line and communicating with said second suction line, said cylinder defining an opening allowing communication between said air chamber and atmosphere, an air intake valve including an air intake valve opening and a valve closing element, said valve closing element being movable to open and close said valve opening to allow and prevent communication between said vacuum chamber and atmosphere, transmission means connected between said control element and said valve element for opening and closing said valve element upon movement of said control element in an opening and closing direction, said transmission means including delay means for delaying the closing of said valve element upon movement of said control element in a closing direction, whereby said control element moves in an opening direction due to a vacuum generated in said vacuum chamber by said suction pump, thereby providing a pulsating suction action at said funnel breast connector, the control element comprises a piston which is arranged axially movable in said cylinder, said transmission means including an axial drive rod connecting the piston element with the closing element of said valve.

7. A breast milk pump according to claim 6, wherein said valve closing element is urged in the closing direction due to the influence of the vacuum in the vacuum chamber and the atmospheric pressure acting on the closing element.

8. A breast milk pump according to claim 6, wherein: said driving rod is movably connected to said piston between a first axial stop and a second axial stop formed in said piston, the distance between said first axial stop and said second axial stop being at least as large as the distance said closing element moves between an open and closed state.

9. A breast milk pump according to claim 8, wherein: said driving rod is connected to a support disc exterior of said cylinder, a spring biasing said support disc to urge said support disc and said closing element into an open state, the spring force influencing the driving rod in the closing element open direction being smaller than the maximum atmospheric pressure acting on the closing element.

10. A breast milk pump according to claim 9, wherein: said air intake valve includes a ceiling ring arranged concentrically with said air intake valve opening, said ceiling ring being positionable on a face of said shutting element, said closing element, including a valve head connected to said driving rod.

11. A breast milk pump according to claim 6 further comprising a return spring positioned in said vacuum chamber bearing against a spring support surface connected to said cylinder and bearing against said piston to urge said piston in the closing direction, said spring support surface being axially repositionable to vary the force of the return spring.

12. A breast milk pump according to claim 6, wherein: said valve including a valve opening and a valve closing element is formed in a shutting element closing said cylinder at said vacuum chamber, said drive rod passing through a central bore formed in said shutting element, said central bore communicating with said valve opening of said valve.

13. A personal pump according to claim 12, wherein: the shutting element of the cylinder includes tube connectors the first connecter connected to said first suction line and said second connector being connected to said second suction line.

14. A breast milk suction pump arrangement comprising: a suction pump having a suction connection; a funnel breast connector; a reservoir connected to said funnel; and a pulsator, said suction pump being connected to said pulsator by a first suction line, said reservoir being connected to said pulsator by a second suction, said pulsator comprising a cylinder, a control element movably positioned in said cylinder and cooperating with said cylinder to define an air chamber and a vacuum chamber, said control element separating said air chamber and said vacuum chamber, said vacuum chamber communicating with said first suction line and communicating with said second suction line, said cylinder defining an opening allowing communication between said air chamber and atmosphere, an air intake valve including an air intake valve opening and a valve closing element, said valve closing element being movable to open and close said valve opening to allow and prevent communication between said vacuum chamber and atmosphere, transmission means connected between said control element and said valve element for opening and closing said valve element upon movement of said control element in an opening and closing direction, said transmission means including delay means for delaying the closing of said valve element upon movement of said control element in a closing direction, whereby said control element moves in an opening direction due to a vacuum generated in said vacuum chamber by said suction pump, thereby providing a pulsating suction action at said funnel breast connector, said delay means includes discharge throttle nozzle positioned in said opening allowing communication between said air chamber and atmosphere and a spring-bias throttle restriction element positioned adjacent said discharge throttle nozzle to bearably restrict the opening of said discharge throttle nozzle.

* * * * *